(12) United States Patent
Fyfe et al.

(10) Patent No.: US 10,060,738 B2
(45) Date of Patent: Aug. 28, 2018

(54) ADHESIVELY COUPLED POWER-METER FOR MEASUREMENT OF FORCE, TORQUE, AND POWER AND ASSOCIATED METHODS

(71) Applicant: 4iiii Innovations Inc., Cochrane (CA)

(72) Inventors: Kipling Fyfe, Cochrane (CA); Keith Wakeham, Calgary (CA)

(73) Assignee: 4iiii Innovations Inc., Cochrane, AB (CA)

( * ) Notice: Subject to any disclaimer, the term of this patent is extended or adjusted under 35 U.S.C. 154(b) by 0 days.

(21) Appl. No.: 15/506,746

(22) PCT Filed: Aug. 26, 2015

(86) PCT No.: PCT/IB2015/002099
§ 371 (c)(1),
(2) Date: Feb. 26, 2017

(87) PCT Pub. No.: WO2016/030768
PCT Pub. Date: Mar. 3, 2016

(65) Prior Publication Data
US 2017/0248420 A1    Aug. 31, 2017

Related U.S. Application Data

(60) Provisional application No. 62/042,208, filed on Aug. 26, 2014.

(51) Int. Cl.
*G01L 1/00* (2006.01)
*G01B 21/32* (2006.01)
*B62M 3/16* (2006.01)
(52) U.S. Cl.
CPC ............... *G01B 21/32* (2013.01); *B62M 3/16* (2013.01); *B62K 2207/00* (2013.01)

(58) Field of Classification Search
CPC ....... G01B 21/32; B62M 3/16; B62K 2207/00
(Continued)

(56) References Cited

U.S. PATENT DOCUMENTS 5,909,781 A    6/1999  Yonekawa et al.
7,461,560 B2  12/2008  Arms et al.
(Continued)

FOREIGN PATENT DOCUMENTS

CN    202106991 U    1/2012
DE      4227586 A1   2/1994
(Continued)

OTHER PUBLICATIONS

International Search Report for PCT/US2017/023454 dated Jul. 18, 2017, 3 pp.
(Continued)

*Primary Examiner* — Max Noori
(74) *Attorney, Agent, or Firm* — Lathrop Gage LLP

(57) ABSTRACT

An adhesively coupled power-meter measures one or more of force, torque, power, and velocity of a mechanical arm. The power meter includes a plate with a first surface prepared for adhesively coupling to the mechanical arm. At least one strain gauge is physically coupled with a second surface, opposite the first, of the plate and with an orientation corresponding to an orientation of the adhesively coupled power meter such that mechanical forces are transferred from mechanical arm to the at least one strain gauge when the plate is adhesively coupled to the mechanical arm. The power meter also includes electronics for receiving a signal from the at least one strain gauge and for determining one or more of force, torque, power and velocity from the signal, and a wireless transmitter for transmitting one or more of force, torque, power and velocity to a receiving device.

18 Claims, 5 Drawing Sheets

(58) Field of Classification Search
USPC .......................................................... 73/781
See application file for complete search history.

(56) References Cited

U.S. PATENT DOCUMENTS

| | | | |
|---|---|---|---|
| 8,316,709 B2 | 11/2012 | Grab | |
| 8,825,279 B2 | 9/2014 | Kitamura et al. | |
| 8,979,758 B2* | 3/2015 | Stein .................... | A61B 5/0031 600/438 |
| 9,417,144 B2 | 8/2016 | Lull et al. | |
| 2005/0285461 A1 | 12/2005 | Kitamura et al. | |
| 2009/0140867 A1* | 6/2009 | Yin ....................... | F17C 13/003 340/626 |
| 2011/0109206 A1 | 5/2011 | Li | |
| 2012/0152020 A1 | 6/2012 | Kim et al. | |
| 2012/0214646 A1 | 8/2012 | Lull et al. | |
| 2012/0330572 A1 | 12/2012 | Longman | |
| 2014/0221160 A1* | 8/2014 | Hardy ................ | A63B 24/0062 482/8 |
| 2016/0072042 A1* | 3/2016 | Fukuda .................... | B62M 3/00 310/338 |

FOREIGN PATENT DOCUMENTS

| | | |
|---|---|---|
| WO | WO 2008/058164 A2 | 5/2008 |
| WO | WO 2016/030768 | 3/2016 |

OTHER PUBLICATIONS

International Search Report with Written Opinion corresponding to International Patent Application No. PCT/IB2015/002099, dated Mar. 10, 2016, 8 pages.

Extended European Search Report for EP 15835668.3 dated Feb. 26, 2018, 8 pp.

* cited by examiner

ADHESIVELY COUPLED POWER-METER FOR MEASUREMENT OF FORCE, TORQUE, AND POWER AND ASSOCIATED METHODS

RELATED APPLICATIONS

This application claims priority to U.S. Patent Application Ser. No. 62/042,208, titled "Adhesively Coupled Power-Meter for Measurement of Force, Torque, and Power and Associated Methods", filed Aug. 26, 2014, and incorporated herein by reference.

BACKGROUND

Cyclists like to know how much effort they are putting into their ride. To add power measurement to a bicycle requires replacement of one or more expensive components.

SUMMARY

Sensors are attached to the inner wall (plate) which may be enclosed, while the other side of the plate is rigidly attached to a mechanical arm within which strain is to be measured. Attaching the plate does not require trained technicians, since the sensors are already affixed to the plate. The plate may be attached to a bicycle crank, a piece of workout equipment, plant machinery, car pieces, or any type of mechanical arm that supports stationary or dynamic loads. The measurements made by the sensors are calibrated with external weights or a load cell. Alternatively, pre-calibrated sensors could be used and their output could be compared against thresholds for notifications/alarms. In the case of a bicycle, this calibration could include hanging weights or applying the load cell to various positions on the pedal spindle. Sensors are arranged such that they are sensitive to bending moments in the mechanical arm. Inertial or magnetic sensors may be used to determine the rotating speed which is combined with the sensed torque to calculate the power, such as input power from a cyclist.

In one embodiment, an adhesively coupled power-meter measures one or more of force, torque, power, and velocity of a mechanical arm. The power-meter includes a plate with a first surface prepared for adhesively coupling to the mechanical arm. At least one strain gauge is physically coupled with a second surface, opposite the first, of the plate and with an orientation corresponding to an orientation of the adhesively coupled power-meter such that mechanical forces are transferred from mechanical arm to the at least one strain gauge when the plate is adhesively coupled to the mechanical arm. The power-meter also includes electronics for receiving a signal from the at least one strain gauge and for determining one or more of force, torque, power and velocity from the signal, and a wireless transmitter for transmitting one or more of force, torque, power and velocity to a receiving device.

In another embodiment, a method measures strain of a mechanical arm using a power-meter adhesively coupled to the mechanical arm. Electronics of the power-meter receive signals from at least one strain gauge that is mechanically coupled to the mechanical arm via a plate of the power-meter. The strain within the mechanical arm is determined based upon the signals and sent to a receiving device.

DETAILED DESCRIPTION OF THE EMBODIMENTS

Figure 1:
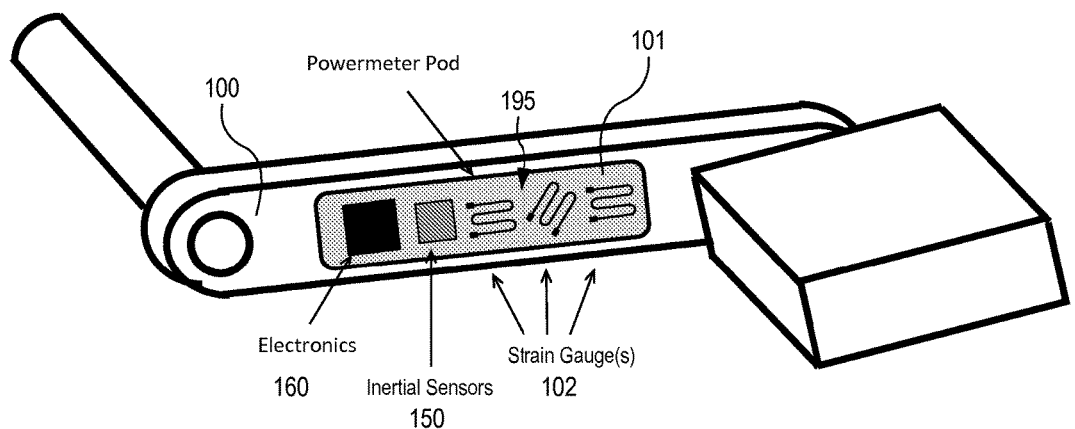
FIG. 1 shows one exemplary adhesively coupled power-meter for measurement of force, torque, and power, in an embodiment.

Fitness training can be accomplished under several different ideologies such as perceived exertion, heart rate, or power output. These ideologies fall under categories of subjective and objective measures of an athlete's effort. Perceived exertion and heart rate are examples of subjective measure that may vary due to fatigue, temperature, hydration, duration of effort, etc. A power-meter, on the other hand, is an objective device that measures both the torque and angular velocity (in a rotating system) or force and velocity (in a translating system) to determine a rate of energy input to a system. This energy rate is generally measured in Watts or horsepower.

Power-meter use has become very popular for training and racing since it objectively displays the power output by an athlete. This objective measure is more desirable than the subjective measures provided by heart rate monitors for example. The user's heart rate changes during a given exertion and this change typically lags strong efforts resulting in inaccurate indications of effort being exerted by the athlete. Thus, subjectively determined measurements have limitations, whereas power-meter measurements are more accurate and provide near instantaneous feedback without bias.

To measure power input to a bicycle for example, there are several locations where the forces, torques, and/or angular velocities may be measured, including shoe cleats, pedals, crank arms, the spider connecting the cranks to the chain ring, chain, wheel hub, and frame. Power measurement at each of these locations presents challenges, requiring specialized instrumentation by skilled technicians on specially engineered components that are specifically designed for attaching the instrumentation.

Bicycle power-meters are not sold with bicycles and are purchased after-market, typically requiring the end user to replace an existing functional piece of hardware with a piece configured with power-meter instrumentation. This approach has two major disadvantages. First, there are a wide variety of brands of bicycle hardware that have varying shapes and sizes. In order to accommodate these varying designs, a power-meter manufacturer has to develop a specific version of the power-meter for use with each brand, and each brand may be required to make custom versions of their component to accommodate the mechanical interface required by the power-meter. For example, most bicycle cranks contain an integrated spider that connects to one or more chain rings. Where instrumentation is incorporated within a spider, the manufacturer must produce a custom version of the crank to allow installation of the instrumented spider. Second, there is significant cost to the end user when purchasing the power-meter, since they are expected to replace an already purchased and likely expensive hardware component of their bicycle in order to accommodate the power-meter.

The power meter embodiments described herein minimize cost and maximize compatibility on bicycle cranks of many makes and models by allowing the power-meter to easily attach to a wide variety of components, such as bicycle cranks, weight equipment in a gym, and industrial machinery.

In one embodiment, the power meter is implemented as a self-contained pod that contains various strain and inertial sensors as well as a controller and wireless transceiver. The pod may be factory installed or installed by an end user to measure one or more of force, torque, acceleration, angular velocity, tangential forces, axial forces, and secondary bending forces (i.e. shear), in any combination. Strain gauges are pre-attached to an interior wall of the pod that is rigidly affixed to the component from which measurements are to be derived. In an alternative embodiment, strain gauges may be directly attached to a crank arm of a bicycle.

Once the pod is attached to the component, the user performs a calibration routine/process/method to determine a relationship between the strain measured on the wall of the pod and a known force applied to the component. Given the known force, the pod may calibrate itself accordingly. For example, an external weight may be applied to the components (or a load cell may be used) and the information of the weight is provided to the pod either directly or through an intermediary device such as one or more of a computer, smartphone, and tablet computer.

FIG. 1 shows one exemplary adhesively coupled power-meter 101 for measurement of force, torque, and power, in an embodiment. Power-meter 101 is implemented as a pod (e.g., a self-contained housing such as housing 302, FIG. 3) containing one or more strain gauges 102, inertial sensors 150, and electronics 160 that include a controller and a wireless transceiver. Inertial sensors 150 may be included within electronics 160 without departing from the scope hereof. Inertial sensors 150 may include one or more of (a) a magnetic reed switch (more for high vibration environments where other inertial sensors may not be applicable), (b) an accelerometer, (c) a gyroscope, and (d) a magnetometer. Inertial sensors 150 may be used alone or in combination for determining rotation of power-meter 101. Electronics 160 may include at least one analog to digital converter for digitizing analog signals for storing and processing.

Power-meter 101 may include a battery (not shown) for powering components therein. Since power meter 101 typically operates wirelessly, operating from power delivered by a self-contained battery, a variety of charging options are possible beside a direct connection such as a USB cable or similar DC charger. For example, power-meter 101 may include one or more of: inductive or pulse coil charging circuitry, a mechanical dynamo, solar power, and energy harvesting from vibration sources. Alternatively, power-meter 101 may include two coils installed on the strain gauges, where the first coil receives an externally applied inductive AC source to power up a strain measuring bridge, and where a second coil transmits the resulting AC signal that is representative of the measured strain. The pulsing and receiving of the inductive energy could be set to the desired sampling rate.

Power-meter 101 is designed for end user installation to measure one or more of force, torque, acceleration, and angular velocity, in any combination. Strain gauges 102 are permanently affixed to an inside wall 195 (herein referred to as the "plate") of the pod, as shown in FIG. 1. However, other orientations for strain gauges 102 may be used without departing from the scope hereof. The pod may include a cover that provides a housing to contain and protect strain gauges 102, inertial sensors 150, and electronics 160 from external elements. The user attaches one outside wall of the pod, corresponding to plate 195 of power-meter 101, to a mechanical arm 100 of a component being measured using adhesive. However, other attachment methods may be used without departing from the scope hereof. The use of adhesive avoids the need to have a specially prepare surface for coupling with strain gauges as required by prior art power-meter devices.

In one embodiment, plate 195 has a tapered edge thickness to reduce shear stresses acting on adhesives at the edge of plate 195. In another embodiment, plate 195 transitions with increasing stiffness using different materials to reduce maximum shear stress in the adhesion layer. In yet another embodiment, plate 195 combines tapering and stiffness transitioning. To reduce shear forces acting on the adhesive (see adhesive 190, FIG. 3), plate 195 may have zigzag edges.

Plate 195 may have optimized surface roughness to improve adhesion between plate and mechanical arm 100. For example, surface roughness of plate 195 may be greater than what would normally be allowable for direct strain gauge application to mechanical arm 100.

In one embodiment, a substrate of strain gauges 102 is thick enough to form plate 195. For example, the substrate of strain gauges 102 may be a thick polyamide layer that forms both the gauge substrate and provides enough structure to act as plate 195.

Plate 195 may be formed to be more sensitive to strains in a certain direction. In one embodiment, plate 195 is formed of sintered plastic that provides directional stiffness. In another embodiment, plate 195 has aligned composite fibers that provide directional stiffness. In another embodiment, plate 195 is formed with vertical honeycomb structures that improve transfer of shear forces and reduce transfer of vertical compression forces, thereby mitigating the effect of surface imperfections on mechanical arm 100.

Plate 195 may be formed with a material that has thermal expansion coefficient similar to mechanical arm 100 to reduce or remove strain caused by differences in expansion rates between plate 195 and mechanical arm 100.

Orientation of one or more of strain gauges 102 is selected to remove effects/coupling from strain/forces that are not of interest (i.e. forces that do not contribute to bending of mechanical arm 100). Although one of strain gauges 102 is shown at an angle of 45 degrees, other angles may be used without departing from the scope hereof. Further, where strain gauges 102 represent multiple strain gauges, these individual strain gauges may be of the same type or of different types (e.g., bend, shear, axial). Additional strain gauges may be included to account for misalignment of plate 195 with respect to direction of interest for strain/force measurements on mechanical arm 100. Misalignment of strain gauges 102, non-orthogonality, and translational errors may be computed during calibration and removed by software based upon signals from multiple strain gauges. Each selected strain gauge may be configured to reduce, remove, and/or cancel unwanted strain that translates into different forces (e.g., shear, axial, bend) and/or thermal effects.

In one embodiment, a thermal conductive pillow (see thermal conductive pillow 196 of FIG. 3) is mounted on top of strain gauges 102 (a) to improve measurement of gauge temperatures and corresponding electronic thermal compensation, (b) to improve dissipation of heat generated by strain gauges 102 during measurement, and (c) is used where the printed circuit board assembly has very uniform thermal dissipation characteristics. In an alternative embodiment, a thermally non-conductive pillow may be used to provide thermal isolation of strain gauges 102 to reduce localized thermal gradients from heat sources near the gauges. For example, the thermally non-conductive pillow may be used where the printed circuit board assembly has components that may create large thermal gradients that impact the strain gauges 102. One or more thermal sensors may be positioned on strain gauges 102 and/or plate 195 to improve temperature measurement accuracy for electronic thermal compensation of measurements. A soft pillow layer may be included to prevent mechanical damage to strain gauges 102 by reducing localized forces on strain gauges 102 and/or plate 195. For example, clamping forces used during installation may be spread over a larger area by a soft pillow to avoid damage to strain gauges 102.

Exemplary Mounting Process

The following provides exemplary steps to ensure that the correct amount of pressure is applied while adhering power-meter 101 to mechanical arm 100. Power-meter 101 may be supplied with elastics that wrap three quarters of the way around mechanical arm 100 and connect to temporary hooks on either side of power meter 101 (e.g., on housing 302). Power meter 101 may be supplied with a spring clamp for use in attaching power meter 101 to mechanical arm 100. A cam may be supplied for use on the backside of mechanical arm 100 (opposite side of power meter 101) that operates to pull on elastic/cable/string attached to tabs on power meter 101 (e.g., housing 302), where the cam allows the user to apply the proper amount of pressure for correct installation of power-meter 101.

Where mechanical arm 100 is made from carbon fiber, the outer layer of paint and/or protective coating may have to be ground down or sanded off to allow adhesive 190 to adhere to a base carbon layer to reduce creep. Another method to deal with creep and fatigue in carbon fiber members is to mount two sets of nearly identical strain gauges, one in a highly stressed region and the other in a lowly stress region on the member. Changes in the linearity of the two sets of gauges may be monitored over time. In carbon materials, highly stressed areas fatigue at higher rates than lower stressed regions, thus changes in the linearity indicate when fatigue is significant.

Creep may be modeled using a non-linear equation, and the zero offset point may be updated in real-time in order to use materials that creep as load cell measuring devices or to determine the current load more reliably.

In one embodiment, power-meter 101 is constructed in two parts: strain gauges 102 are located in one part and the electronics are located in the other part. The part containing strain gauges 102 could then be installed during the manufacturing of the bicycle/machine and the other part (containing the electronics) could be sold as an add-on at the time of purchase or later. With this embodiment, a type of strain gauge and associated pre-calibration information could be indicated by methods such as QR code, bar code, NFC, serial number, RFID or other electronic means. This gauge type and calibration information could be encoded directly in the above mentioned identification means or stored in a database in the matching part (containing the electronics), or in a smartphone or Internet database.

In another embodiment, strain gauges 102 are embedded and/or molded into carbon and/or fiberglass material of mechanical arm 100. This could be performed either during the molding process of the raw material forming mechanical arm 100, or strain gauges 102 may be applied on top of the cured material forming mechanical arm 100 before any paint/protective process is applied. The layer of carbon for mounting strain gauges 102 could be selected to give the desired sensitivity characteristics for strain gauges 102. For example, strain gauges 102 may be positioned to have most sensitivity in the direction of the fiber, perpendicular to it, or at some arbitrary angle to it.

There are many methods for affixing strain gauges—epoxy, ultrasonic welding, welding, posts, glue, resin, cyanoacrylite, thermal plastic bonding agents, ultrasonic welding, etc. When strain gauges 102 and/or electronics 160 are applied to plate 195, they may be covered in a coating (e.g., adhesive or other such protective coating) for waterproofing, protecting the components and to keep them at a uniform temperature.

In another embodiment, power-meter 101 in its entirety is mounted and/or molded directly into mechanical arm 100.

Where power-meter 101 is to be attached by an end user, power-meter 101 may be supplied with a portable sand blaster for use in preparing a surface of mechanical arm 100 prior to attachment of power-meter 101. The portable sand blaster may use compressed gases from a small cartridge to propel abrasive particles (e.g. sand) at high velocities. For example, the compressed gas could come from a common bicycle CO2 cartridge. A small mechanical enclosure may be used to capture/isolate the abrasive particles such that only the desired area on the surface of mechanical arm 100 is cleaned or sand blasted. The enclosure may have a vent to release used compressed gasses without releasing abrasive particles to the external environment. For example, a filter material or cyclonic isolation may be used to retain the abrasive particles within the enclosure.

Figure 2:
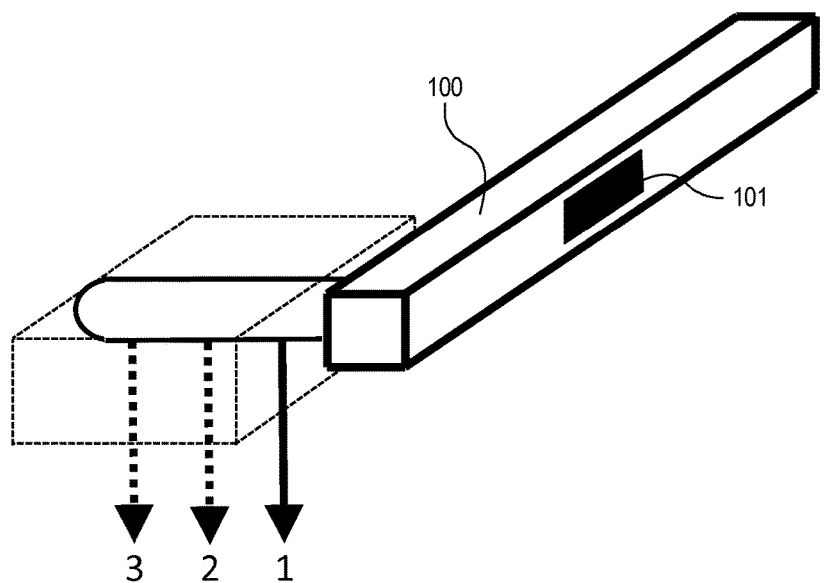
FIG. 2 shows exemplary calibration of the power-meter of FIG. 1 after it is installed on a mechanical arm.

FIG. 2 shows exemplary calibration of power-meter 101 after it is installed on mechanical arm 100. Since power-meter 101 may be attached by the user, to determine a relationship between force and/or torque sensed by power-meter 101 and actual input force and/or torque to mechanical arm 100, a calibration method is employed. During this calibration method, a load cell and/or one or more suspended weights are used to apply a known force and/or torque to mechanical arm 100. The known force and/or torque is input to power-meter 101, wherein electronics 160 determine one or more calibration factors that allow power-meter 101 to determine subsequent forces and/or torques applied to mechanical arm 100 based upon sensed values from strain gauges 102. Advantageously, this calibration method is simple and can be performed without complicated equipment and without removal of the component from the user's apparatus (e.g., bicycle). Advantageously, the user may recalibrate power-meter 101 at any time.

Figure 3:
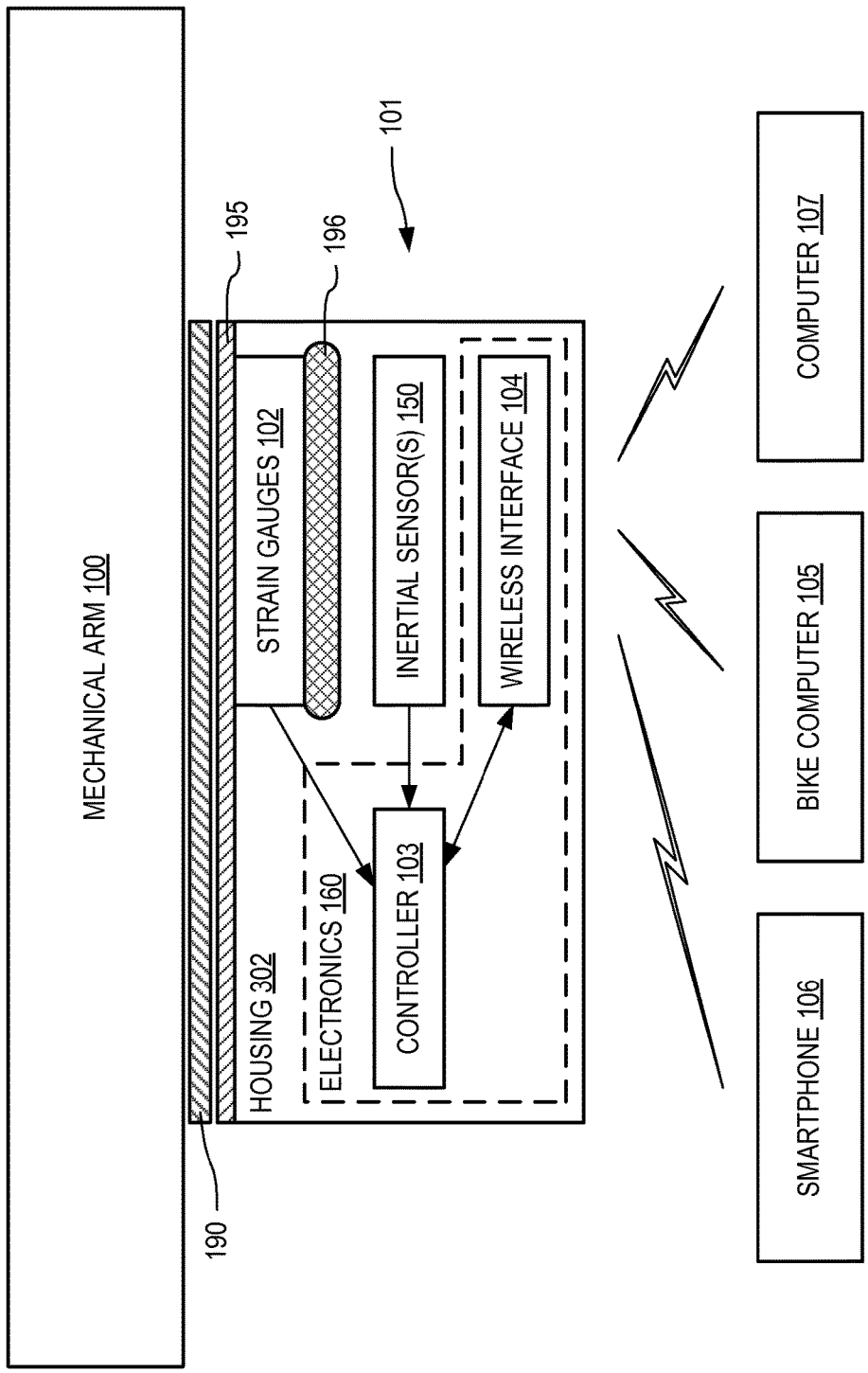
FIG. 3 is a schematic showing the power-meter of FIG. 1 in further exemplary detail, in an embodiment.

FIG. 3 is a schematic showing power-meter 101 in further exemplary detail. Power-meter 101 is shown attached to mechanical arm 100 by an adhesive 190. Bending and/or torque present in mechanical arm 100 is sensed by strain gauges 102 and input to a controller 103 within electronics 160. Electronics 160 may include other signal processing components (not shown for clarity of illustration).

Adhesive 190 is selected to have a shear strength that is at least as high as the largest expected shear experienced between mechanical arm 100 and plate 195 (i.e., power meter 101). In an alternative embodiment, welding is used in place of adhesive 190. For example, strain gauges 102 may be welded at their edges or specific points to plate 195, and the specific points and welding pattern may be selected to reduce or remove unwanted forces. Welding may utilize one or more of ultrasonic welding, laser welding, capacitive discharge welding, and so on.

Controller 103 includes software and performs calculations to determine one or more of force, torque, and power applied to mechanical arm 100. Electronics 160 includes a wireless interface 104 that, under control of controller 103, communicates determined force, torque, and/or power to a receiving device, such as a bike computer 105, a smartphone/tablet 106, and a computer 107. Computer 107 is for example a general purpose processor. Wireless interface 104 may implement one or more known communication protocols to establish one way or bidirectional communications with devices 105, 106, and/or 107. In an alternate embodiment, data is transferred from power-meter 101 to an external processor (e.g., within one or more of bike computer 105, smartphone/tablet 106, and computer 107) for processing. For example, power-meter 101 may partially process data from strain gauges 102 and/or inertial sensors 150, and send the partially processed data to the external processors for further processing.

In one example of operation, power-meter 101 determines one or more of force, torque and power applied to a drive train of the bicycle by a cyclist. This drive train includes a first and second crank arm, each engaged by the cyclist at an outboard end. An inboard end of each crank arm is rotatably mounted to the bicycle at a bottom bracket of the bicycle. At least one chain ring is configured to rotate a driven wheel of the bicycle. Power-meter 101 may be installed (as shown in FIG. 1) on the side of the first or second crank arm or two power-meters 101 may be installed, one on each of the first and second crank arms. Once the power-meter 101 is installed on the crank arm, a load cell (or weight) is to be connected to the outboard end such that a relationship between the strain measured in power-meter 101 and the load provided by the load cell may be determined. Further, various weights and offsets may be applied to the outboard end of the crank arm to increase the accuracy of the determined relationship.

In another example of operation, power-meter 101 operates to determine 'strain' along with existing forces, torque, and power, as described above. Power may be determined for both rotational as well as translational acceleration and/or motion. Rotational power is determined as a product of measured torque and angular velocity. Translational power is determined as a product of force (measured from strain gauges) and velocity (obtained by integrating acceleration, for example).

Measurement accuracy is of concern especially when power-meter 101 is calibrated by the user. Power-meter 101 contains multiple strain gauges 102 to reduce error in measurement. Conventional power measurement uses only bending measurements on a mechanical arm. In one embodiment, multiple strain gauges 102 are oriented for measuring bending, torsion, and axial forces along the longitudinal length of mechanical arm 100 (e.g., the crank arm). Typically, the cyclist may vary force applied to the crank arm by twisting their ankle, or by applying more force closer inboard or further outboard depending on the style of riding, which may also vary throughout a ride. By measuring both bending and torsion (torque), power-meter 101 determines a more accurate measurement of power applied to the power train.

In one embodiment, a shear strain gauge positioned at 45 degrees to the longitudinal length of the crank arm shows a summation of shear forces caused by bending and torsion (see the strain gauge orientations in FIG. 1). By utilizing multiple calibration points with different offsets (see labels 1, 2 and 3 in FIG. 2), and/or by applying different weights, power-meter 101 determines the influence of this torsion on the bending of mechanical arm 100, and thereby compensates when determining force, torque, and/or power. Accuracy of power-meter 101 is thereby increased by using results from multiple tests.

Power-meter 101 may be used to measure force, torques, and/or power in mechanical arms and other members used in industrial applications. Plate 195 within power-meter 101 has negligible impact on the accuracy of measurement when power-meter 101 is applied to mechanical arm 100 of sufficient thickness. Thus, power-meter 101 may be used for collecting and wirelessly transmitting strain data over time to any device with an appropriate receiver.

Electronics 160 may include a memory buffer for temporarily storing high speed data from strain gauges 102 and inertial sensors 150. This allows controller 103 to process the stored data at a later time and/or to reduce the duration that controller 103 is actively powered to receive sensor data from the various inertial sensors (e.g., magnetic reed switches, accelerometers, etc.), and strain gauges 102.

In certain embodiments, plate 195 is matched to the material of mechanical arm 100 by taking into account material properties such as thermal expansion coefficients. For connecting to a carbon fiber or glass fiber application, plate 195 may be a non-metallic material with similar expansion coefficients such that no thermal strain is induced due to the differential of expansion coefficients. Thus plate 195 may be made from identical material or similar material to the underlying base material of mechanical arm 100. In an alternative embodiment, calibration of power-meter 101 is used to remove material inconsistencies, for example by testing/calibrating at various temperatures or by using properties of different materials. Power-meter 101 may also include a temperature sensor to measure temperature within the power-meter. In one example of operation, temperature is sensed during calibration and stored together with calibration data within power-meter 101 (or optionally within a connected device). When a measurement is subsequently made, temperature is again sensed, and used to adjust calculated values thereby improving accuracy of power-meter 101. In one embodiment, power-meter 101 may determine the effects of temperature on measurements, and thereafter compensate for temperature errors within materials and sensors.

In certain applications, the material used for plate 195 is selected such that it is less stiff than the material that it is being attached to (i.e., mechanical arm 100) such that power-meter 101 does not greatly affect the stiffness of mechanical arm 100. Thus, the response of power-meter 101 may be considered to be only the response of mechanical arm 100.

Power-meter 101 may utilize inertial sensors 150 (e.g., an accelerometer) to determine a rotating speed of the mechanical arm that may be utilized within controller 103, in combination with the sensed torque, to calculate an input power to mechanical arm 100 (e.g., from a cyclist). Power-meter 101 may also utilize a magnet and reed switch, and/or other similar sensors, to measure the rotating speed.

More than one power-meter 101 may be used together, wherein these power-meters may cooperate and communicate to determine power within a more complicated system.

For example, where two power-meters 101 are each coupled to a different one of the left and right crank arm of a bicycle, communication from each of these left and right power-meters 101 may be used together and individually to determine power provided by the cyclist to each of the left and right crank arms and collectively. In one example of operation, power calculated from each of the left and right power-meters is summed to determine the total power received from the cyclist.

In an alternative embodiment, power-meter 101 is mechanically coupled to mechanical arm 100, such as by clamping, clipping, and other similar means known in the art.

In yet another alternate embodiment, power-meter 101 utilizes a single strain gauge 102 for determining one or more of force, torque, and power.

Figure 4:
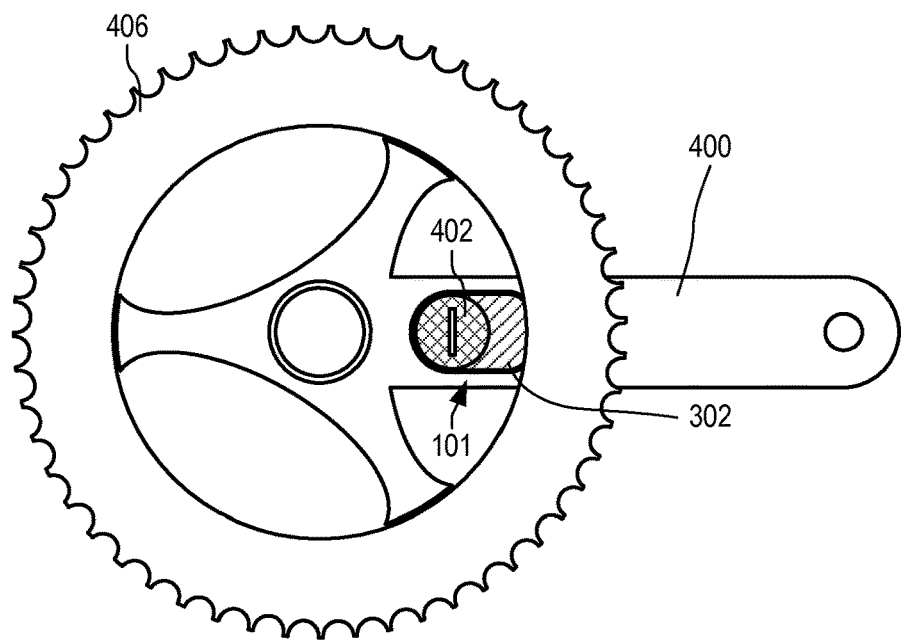
FIG. 4 shows the adhesively coupled power meter of FIG. 1 coupled to a crank arm driving a circular chain ring, in an embodiment.

FIG. 4 shows adhesively coupled power-meter 101 of FIG. 1 coupled to a crank arm 400 driving a circular chain ring 406. Housing 302 adhesively attaches to crank arm 400 as shown and operates to measure power applied to crank arm 400. Housing 302 is shown with a removable battery cover 402.

Figure 5:
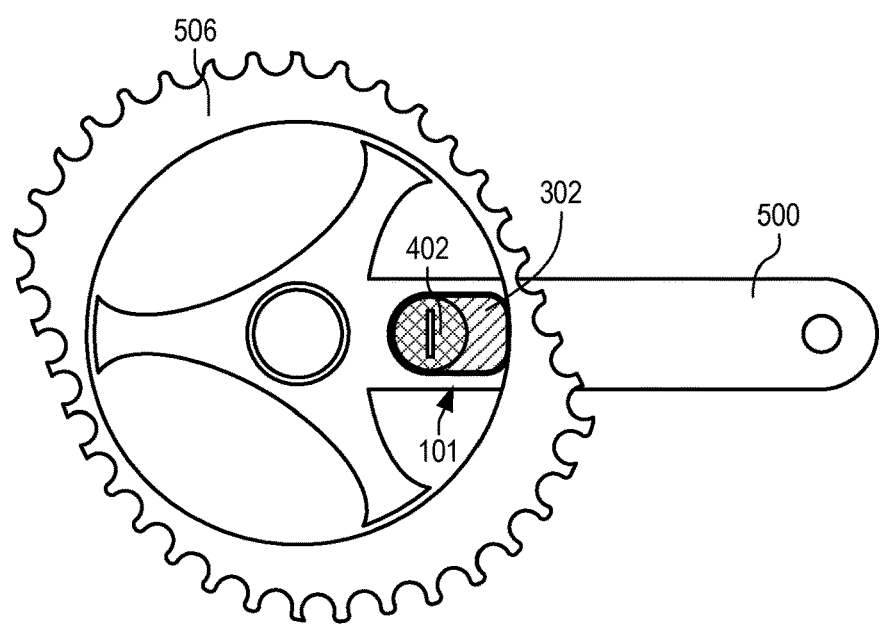
FIG. 5 shows the adhesively coupled power meter of FIG. 1 coupled to a crank arm driving a non-circular chain ring, in an embodiment.

FIG. 5 shows adhesively coupled power-meter 101 of FIG. 1 coupled to a crank arm 500 driving a non-circular chain ring 506 (e.g., a Q or oval chain ring). Housing 302 adhesively attaches to crank arm 500 as shown and operates to measure power applied to crank arm 400. Housing 302 is shown with a removable battery cover 402.

Figure 6:
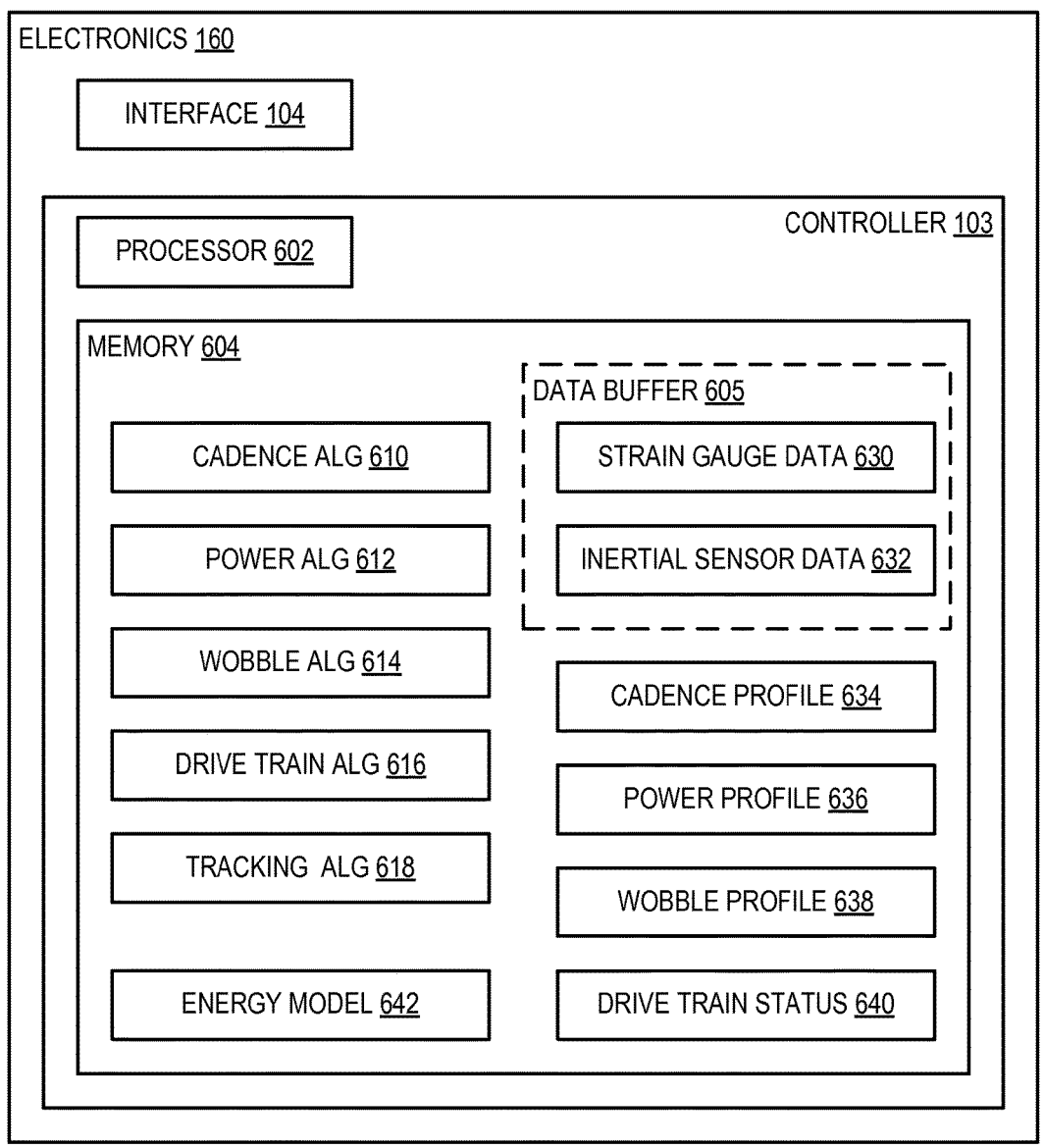
FIG. 6 shows the electronics of the adhesively coupled power meter in further exemplary detail.

FIG. 6 shows electronics 160 in further exemplary detail, illustrating exemplary algorithms used within power-meter 101. Electronics 160 are shown with interface 104 and controller 103. Controller 103 is shown with a processor 602 and a memory 604. Interface 104 is a wireless interface, implementing one or more protocols selected from the group including Bluetooth™, Ant+, ZigBee, and so on. Memory 604 includes a data buffer 605 that periodically receives strain gauge data 630 from strain gauges 102 and inertial sensor data 632 that is periodically received from inertial sensors 150. Data buffer 605 is for example implemented as a cyclic buffer for temporarily storing measurements from strain gauges 102 and inertial sensors 150.

Memory 604 is shown also storing a cadence algorithm 610, a power algorithm 612, a wobble algorithm 614, a drive train algorithm 616, and a tracking algorithm 618, each of which has machine readable instructions that are executable by processor 602 to provide the functionality described herein.

Cadence algorithm 610 analyzes one or both of strain gauge data 630 and inertial sensor data 632 to determine a cadence profile 634 (e.g., rotation rate and variances thereof over time) of crank arm 100, 400, 500. Cadence algorithm 610 may also perform intra-revolution analysis of data 630, 632 to track changes in speed and cycling efficiency. For example, cadence algorithm 610 may analyze inertial sensor data 632 received from a plurality of inertial sensors 150 configured with adhesively coupled power meter 101. Alternatively, or in addition to this, more direct sensors, including, but not limited to potentiometers, optical and magnetic based sensors could be employed within adhesively coupled power meter 101 and used by cadence algorithm 610. Cadence profile 634 is for example transmitted via interface 104 to one or more of smartphone 106, bike computer 105, and computer 107 for display to a user in numerical and/or graphical form.

Figure 7:
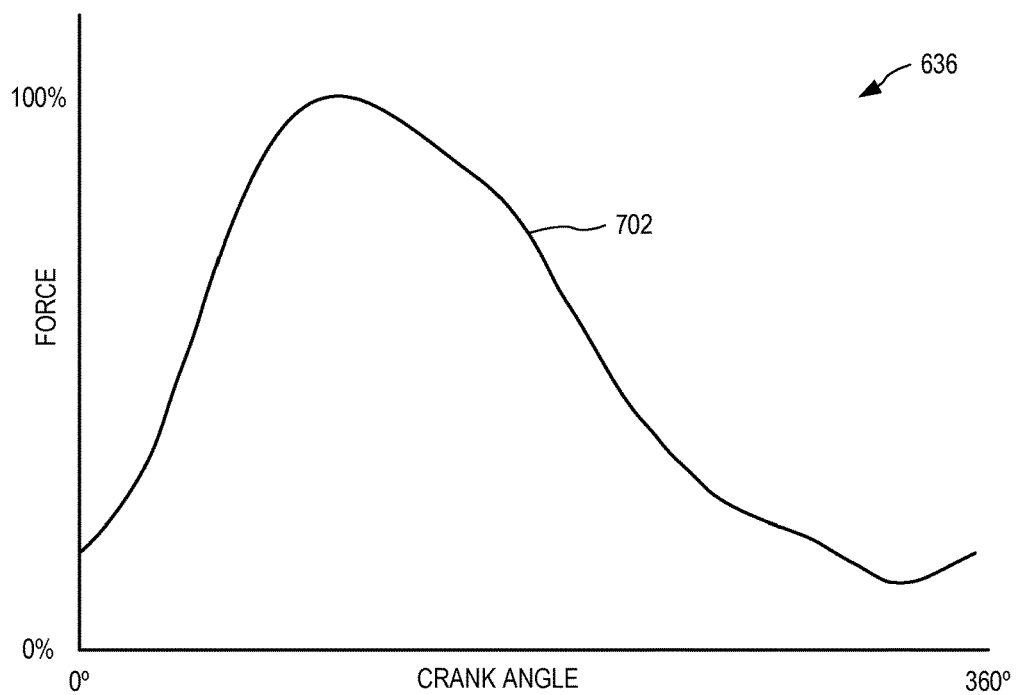
FIG. 7 shows one exemplary power profile generated by the power algorithm of the adhesively coupled power meter of FIG. 1, in an embodiment.

Power algorithm 612 analyzes strain gauge data 630 and optionally inertial sensor data 632 and generates power profile 636. FIG. 7 shows one exemplary power profile 636 generated by power algorithm 612. In the example of FIG. 7, power profile 636 shows a line 702 representing force applied to crank arm 500, and thereby non-circular chain ring 506, for one complete revolution. Power algorithm 612 may generate power profile 636 using statistical techniques calculated from multiple consecutive rotations of crank arm 500. Power profile 636 is for example transmitted via interface 104 to one or more of smartphone 106, bike computer 105, and computer 107 for display to a user in numerical and/or graphical form. Where computer 107 receives data from two adhesively coupled power meters 101, each attached to a different crank arm of the same bicycle, power algorithm 612 may generate power profile 636 with two graphs, or two lines, where each line represents power applied to a different one of the crank arms, thereby allowing the cyclist to compare power input by each leg.

Figure 8:
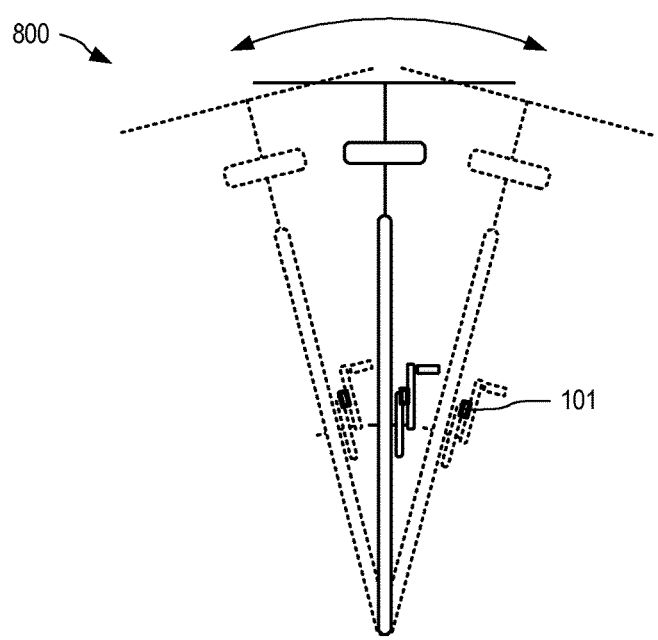
FIG. 8 is a rear view of a portion of a bicycle with the adhesively coupled power meter of FIG. 1, illustrating lateral movement of the bicycle when pedaled.

Wobble algorithm 614 analyzes strain gauge data 630 and inertial sensor data 632 to generate a wobble profile 638 to show lateral (side to side motion). FIG. 8 is a rear view of a portion 800 of a bicycle with at least one adhesively attached power meter 101 of FIG. 1, illustrating lateral movement of the bicycle when pedaled. Wobble algorithm 614 isolates the lateral motion from strain gauge data 630 and inertial sensor data 632 and generates wobble profile 638 to show the determined lateral motion. Wobble profile 638 is for example transmitted via interface 104 to one or more of smartphone 106, bike computer 105, and computer 107 for display to a user in numerical and/or graphical form.

Drive train algorithm 616 analyzes inertial sensor data 632, and optionally strain gauge data 630, over time to determine one or more of vibration, losses from drivetrain alignment, wear, and so on, and generates a drive train status 640. Drive train status 640 is for example transmitted via interface 104 to one or more of smartphone 106, bike computer 105, and computer 107 for display to a user in numerical and/or graphical form.

Tracking algorithm 618 analyzes inertial sensor data 632 and strain gauge data 630 over time and generates an energy model 642 based upon determined input power provided by the cyclist, and estimated spend power based upon one or more of: an anemometer or similar device for estimating wind resistance, an inclinometer for measuring a grade of the terrain being traversed, and a pressure sensor built into the tube/tire to estimate the rolling resistance of the bicycle.

Tracking algorithm 618 may also compare other sensed static and dynamic components (e.g., loads on the crank arms and/or the bicycle frame and/or the seat post of the bicycle using additional sensors where necessary) to determine whether the rider is sitting or out of the saddle.

In one example of use, where each cycle in a group training session has at least one adhesively attached power-meter 101, power profiles 636 determined from each of the adhesively attached power-meters 101 can be used to calculate slipstream efficiency. For each individual rider, the power levels indicated when riding at the front of the group may be compared to the power levels indicated when drafting behind various members in their group.

Where adhesively attached power meter 101 is attached to an electrically assisted bicycle, power profile 636 as input by the rider may be compared to power provided by the battery/motor of the cycle.

In one embodiment, adhesively coupled power meter 101 transmits partially processed signals from one or more of strain gauges 102 and inertial sensors 150 to one or more of bike computer 105, smartphone 106, and computer 107. Each of bike computer 105, smartphone 106, and computer 107 may implement one or more of algorithms 610, 612,

614, 616, 618, and energy model 642 to generate profiles and status similar to profiles 634, 636, 638 and status 640.

Other Uses

Power-meter 101 may be used for other applications, including:

- Skis (Nordic/classic or skate skis, used to measure flex and engagement for coaching or virtual coaching feedback)
- Boat oars for competitive rowing
- Paralyrnpic triathlon, both bike and wheelchair stage
- Instrumentation of ice skates
- Weightlifting for accurate determination of weight on the barbell/dumbbell
- Weight machines to determine the number of reps and the amount of force applied
- Motorsports
  - Could be used in any variety of applications from drive shaft and half shaft loadings, to instrumentation of the large spokes on a wheel to determine wheel horsepower
  - Determination of suspension forces
  - Determination of hull stresses for boat racing (hydroplane races, F1 Powerboat, etc.)
  - Determination of live down force for telemetry of wings
  - Determination of down force and drag force on adjustable wings for use in controllers
- Horse training—can be used inline on a device reigns to allow students learning to ride to adjust forces
- A shoe to determine kicking or impact force,
- Measurement of forces, torques, moments, resonant frequencies in:
  - racquet/stick sports: hockey, golf, lacrosse, baseball, tennis, fencing, racquet ball, squash, table tennis, etc.
  - paddles/oars: kayak, paddling, rowing
- Weight machines and aerobic workout machines—measuring force, number of repetitions, speed and real-time power.
- Instrumentation of free weights: dumbbells and barbells to determine number of repetitions, speed and real-time power.
- Impact force measurement: shoes (impact/heel strike), helmets, protective padding.
- If a combination of strain gauges (or other strain sensing elements) are used in conjunction with motion sensing devices (e.g. inertial sensors like accelerometers and gyros) a model of the dynamics of the system could be constructed. In this manner, tuning of the system (the man/machine interface) would be possible. For example an optimal racquet/club could be chosen/designed for an individual. The same set of tools could be used to tune the resonant frequency of the object.
- If the pods are being used to measure the force in a member that is translating (instead of rotating), the velocity of the member could be estimated by a plurality of means including, but not limited to GPS, anemometer, pitot tube, inertial sensors, counting of wheel revolutions, etc. From the force and velocity estimate, the power could be determined.
- Application of multiple load cells on a member would enable one to detect forces, moments, shear and torque about any axis of the member.
- Applications in the transportation industry: measurement of dynamic forces on drive shafts (for power determination or stress analysis), suspension members, frame elements and external forces (e.g. the downward force on a car spoiler).
- In manufacturing applications, this force measurement pod could be used to measure cutting or punching forces (i.e. robotic stamping, die cutting). In this way, the operator would know when to sharpen/replace the tool or adjust the system.
- In condition monitoring applications, the health and applied loads of a structure could be determined from acceleration/vibration measurements and associated strains measured in the structure.
- Instead of performing all the power processing on the pod, raw strain data or partially processed data could be exported off of the pod to be processed by some external device in real-time or offline.

The invention may also be used in industrial applications, including:

- Couplings between rail cars or transport trucks, force× linear speed=power in watts transferred through, could be used to determine aerodynamic drag on trains or other shipping units which have a coupling, could also be used to determine forces alone.
- Measure the stress and bending moments in arbitrary mechanical members.

Combination of Features

Features described above as well as those claimed below may be combined in various ways without departing from the scope hereof. The following examples illustrate possible, non-limiting combinations the present invention has been described above, it should be clear that many changes and modifications may be made to the process and product without departing from the spirit and scope of this invention:

(A) An adhesively coupled power-meter for measurement of one or more of force, torque, power, and velocity of a mechanical arm, includes a plate having a first surface prepared for adhesively coupling with the mechanical arm, at least one strain gauge physically coupled with a second surface of the plate opposite the first and with an orientation corresponding to an orientation of the adhesively coupled power meter, wherein mechanical forces are transferred from mechanical arm to the at least one strain gauge when the plate is adhesively coupled to the mechanical arm, electronics for receiving a signal from the at least one strain gauge and for determining one or more of force, torque, and power from the signal, and a wireless transmitter for transmitting, to a receiving device, one or more of force, torque, and power.

(B) In the system denoted as (A), further including at least one inertial sensor for sensing movement of the mechanical arm, wherein the electronics determine power based upon sensed force and sensed movement.

(C) In either of the systems denoted as (A) and (B), the electronics determining at least angular velocity of the mechanical arm based upon the sensed movement.

(D) In any of the systems denoted as (A) through (C), the at least one inertial sensor being selected from the group consisting of a magnetic reed switch, an accelerometer, a gyroscope, and a magnetometer.

(E) In any of the systems denoted as (A) through (D), the at least one strain gauge being oriented to reduce sensitivity to forces, moments and torques in the mechanical arm that are not of interest.

(F) In any of the systems denoted as (A) through (E), the at least one strain gauge being oriented at an angle relative to other of the at least one strain gauge.

(G) In any of the systems denoted as (A) through (F), the plate being formed to be more sensitive to strains in a certain direction.

(H) In any of the systems denoted as (A) through (G), the plate having aligned composite fibers that provide directional stiffness.

(I) In any of the systems denoted as (A) through (H), the plate being formed of sintered plastic to provide directional stiffness.

(J) In any of the systems denoted as (A) through (I), the plate being formed of vertical honeycomb structures that improve transfer of shear forces and reduce transfer of vertical compression forces, thereby mitigating the effect of surface imperfections on the mechanical arm.

(K) In any of the systems denoted as (A) through (J), the plate having a tapered edge thickness to reduce shear stresses acting on adhesive at the edge of plate.

(L) In any of the systems denoted as (A) through (K), the plate transitioning with increasing stiffness using different materials to reduce maximum shear stress in the adhesive.

(M) In any of the systems denoted as (A) through (L), the plate having zigzag edges to reduce shear forces acting on the adhesive.

(N) In any of the systems denoted as (A) through (M), the plate forming a substrate of the at least one strain gauge.

(O) In any of the systems denoted as (A) through (N), the plate being a polyamide layer that forms both a substrate of the at least one strain gauge and provides structure to directly couple with the mechanical arm.

(P) In any of the systems denoted as (A) through (O), the plate being formed of a material that has substantially the same thermal expansion coefficient as the mechanical arm.

(Q) In any of the systems denoted as (A) through (P), orientation of the one or more of strain gauges being selected to remove the effects/coupling from strain/forces that do not contribute to bending of the mechanical arm.

(R) A method for measuring strain of a mechanical arm using a power-meter adhesively coupled to the mechanical arm, including receiving, within electronics of the power-meter, signals from at least one strain gauge that is mechanically coupled to the mechanical arm via a plate of the power meter, determining the strain within the mechanical arm based upon the signals, and sending the strain to a receiving device.

(S) In the method denoted as (R), further including receiving a second signal from at least one inertial sensor mechanically coupled to the mechanical arm, determining one or more of force and torque based upon the strain, determining velocity of the mechanical arm based upon the second signal, and calculating power applied to the mechanical arm based upon one or more of the determined force, the determined torque, and the determined velocity.

(T) In either of the methods denoted as (R) and (S), further including self-calibrating the force measurement based upon a known force applied to the mechanical arm.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An adhesively coupled power-meter for measurement of one or more of force, torque, power, and velocity of a mechanical arm, comprising:
    a plate having a first surface prepared for adhesively coupling with the mechanical arm;
    at least one strain gauge physically coupled with a second surface of the plate opposite the first and with an orientation corresponding to an orientation of the adhesively coupled power meter, wherein mechanical forces are transferred from mechanical arm to the at least one strain gauge when the plate is adhesively coupled to the mechanical arm;
    electronics for receiving a signal from the at least one strain gauge and for determining one or more of force, torque, and power from the signal; and
    a wireless transmitter for transmitting, to a receiving device, one or more of force, torque, and power;
    wherein orientation of the one or more of strain gauges is selected to remove one or more of the effects, coupling from strain, and forces that do not contribute to bending of the mechanical arm.

2. The adhesively coupled power-meter of claim 1, further comprising at least one inertial sensor for sensing movement of the mechanical arm, wherein the electronics determine power based upon sensed force and sensed movement.

3. The adhesively coupled power-meter of claim 2, wherein the electronics determine at least angular velocity of the mechanical arm based upon the sensed movement.

4. The adhesively coupled power-meter of claim 2, the at least one inertial sensor being selected from the group consisting of a magnetic reed switch, an accelerometer, a gyroscope, and a magnetometer.

5. The adhesively coupled power-meter of claim 1, wherein the at least one strain gauge is oriented to reduce sensitivity to forces, moments and torques in the mechanical arm that are not of interest.

6. The adhesively coupled power-meter of claim 1, wherein the at least one strain gauge is oriented at an angle relative to other of the at least one strain gauge.

7. The adhesively coupled power-meter of claim 1, wherein the plate is formed to be more sensitive to strains in a certain direction.

8. The adhesively coupled power-meter of claim 1, wherein the plate has aligned composite fibers that provide directional stiffness.

9. The adhesively coupled power-meter of claim 1, wherein the plate is formed of sintered plastic to provide directional stiffness.

10. The adhesively coupled power-meter of claim 1, wherein the plate is formed of vertical honeycomb structures that improve transfer of shear forces and reduce transfer of vertical compression forces, thereby mitigating the effect of surface imperfections on the mechanical arm.

11. The adhesively coupled power-meter of claim 1, wherein the plate has a tapered edge thickness to reduce shear stresses acting on adhesive at the edge of plate.

12. The adhesively coupled power-meter of claim 1, wherein the plate transitions with increasing stiffness using different materials to reduce maximum shear stress in the adhesive.

13. The adhesively coupled power-meter of claim 1, wherein the plate has zigzag edges to reduce shear forces acting on the adhesive.

14. The adhesively coupled power-meter of claim 1, wherein the plate forms a substrate of the at least one strain gauge.

15. The adhesively coupled power-meter of claim 14, wherein the plate is a polyamide layer that forms both a substrate of the at least one strain gauge and provides structure to directly couple with the mechanical arm.

16. The adhesively coupled power-meter of claim 1, wherein the plate is formed of a material that has substantially the same thermal expansion coefficient as the mechanical arm.

17. A method for measuring strain of a mechanical arm using a power-meter adhesively coupled to the mechanical arm, comprising the steps of:
- receiving, within electronics of the power-meter, signals from at least one strain gauge that is mechanically coupled to the mechanical arm via a plate of the power meter;
- determining the strain within the mechanical arm based upon the signals;
- sending the strain to a receiving device;
- receiving a second signal from at least one inertial sensor mechanically coupled to the mechanical arm;
- determining one or more of force and torque based upon the strain;
- determining velocity of the mechanical arm based upon the second signal; and
- calculating power applied to the mechanical arm based upon one or more of the determined force, the determined torque, and the determined velocity.

18. A method for measuring strain of a mechanical arm using a power-meter adhesively coupled to the mechanical arm, comprising the steps of:
- receiving, within electronics of the power-meter, signals from at least one strain gauge that is mechanically coupled to the mechanical arm via a plate of the power meter;
- determining the strain within the mechanical arm based upon the signals;
- sending the strain to a receiving device; and
- self-calibrating the force measurement based upon a known force applied to the mechanical arm.

* * * * *